(12) United States Patent
Rosenberg

(10) Patent No.: US 10,722,335 B1
(45) Date of Patent: Jul. 28, 2020

(54) DEVICE FOR THE DELIVERY OF A PROSTHETIC IMPLANT AND METHOD OF USE THEREOF

(71) Applicant: Proximate Concepts LLC, Fort Lee, NJ (US)

(72) Inventor: Paul Rosenberg, Saddle River, NJ (US)

(73) Assignee: Proximate Concepts LLC, Fort Lee, NJ (US)

( * ) Notice: Subject to any disclaimer, the term of this patent is extended or adjusted under 35 U.S.C. 154(b) by 0 days.

(21) Appl. No.: 16/047,757

(22) Filed: Jul. 27, 2018

Related U.S. Application Data

(63) Continuation-in-part of application No. 15/898,537, filed on Feb. 17, 2018, which is a continuation of application No. 15/352,079, filed on Nov. 15, 2016, now Pat. No. 9,925,028.

(51) Int. Cl.
*A61F 2/12* (2006.01)
*A61F 2/00* (2006.01)
*A61B 90/00* (2016.01)
*A61L 31/14* (2006.01)

(52) U.S. Cl.
CPC ............ *A61F 2/0059* (2013.01); *A61B 90/02* (2016.02); *A61F 2/12* (2013.01); *A61F 2220/005* (2013.01); *A61F 2220/0083* (2013.01); *A61F 2230/0067* (2013.01); *A61F 2250/005* (2013.01); *A61F 2250/0056* (2013.01);
(Continued)

(58) Field of Classification Search
CPC ........................................................ A61F 2/12
USPC ........................................................ 623/7–8
See application file for complete search history.

(56) References Cited

U.S. PATENT DOCUMENTS

| 279,555 A | 6/1883 | Fish |
| 426,165 A | 4/1890 | Brittin |
| 568,411 A | 9/1896 | Pratt |

(Continued)

FOREIGN PATENT DOCUMENTS

| CN | 201076483 Y | 6/2008 |
| FR | 2733903 A1 | 11/1996 |

(Continued)

OTHER PUBLICATIONS

Extended European Search Report for European Patent Application No. 17197722.6 dated Apr. 11, 2018. 9 pages.

(Continued)

*Primary Examiner* — Suzette J Gherbi
(74) *Attorney, Agent, or Firm* — Leason Ellis LLP

(57) ABSTRACT

A surgical device for assisting in the placement of a prosthetic implant. One or more sheets of polymer are in the form of a conical frustum such that a proximal end is sealed and a distal end is open, with an elongated slit extending from the distal end toward the proximal end. A single opening is formed by the distal opening and the elongated slit with a set of inter-lockable fastener elements disposed along opposing sides and configured to seal the elongated slit such that the distal end remains open to allow for egress of the prosthetic implant for placement into a surgical pocket. A lubricious coating is applied to the interior cavity of the frustum in addition to one or more surface active coatings. Movement of the prosthetic implant across the one or more surface active coatings causes the coatings to provide one or more offered benefits.

17 Claims, 10 Drawing Sheets

(52) U.S. Cl.
CPC .............. *A61F 2250/0069* (2013.01); *A61F 2250/0097* (2013.01); *A61L 31/145* (2013.01)

(56) References Cited

U.S. PATENT DOCUMENTS

| | | | |
|---|---|---|---|
| 1,409,544 A | 3/1922 | Hallock | |
| 1,486,078 A | 3/1924 | Dumont | |
| 1,612,383 A | 12/1926 | Lepeshkin | |
| 2,935,241 A | 5/1960 | Brady | |
| 3,138,821 A | 6/1964 | Macciocchi et al. | |
| 3,156,240 A | 11/1964 | Harrison et al. | |
| 3,157,312 A | 11/1964 | Kitterman | |
| 3,324,906 A | 6/1967 | Chu | |
| 3,769,971 A | 11/1973 | Collins | |
| 3,883,902 A | 3/1975 | Lynch | |
| 4,035,850 A | 7/1977 | Cresswall | |
| 4,143,428 A | 3/1979 | Cohen | |
| 4,358,028 A | 11/1982 | Chiquiar-Arias | |
| 4,641,648 A * | 2/1987 | Shapiro | A61B 90/00 606/1 |
| 4,650,833 A | 3/1987 | Sakagami et al. | |
| 4,955,906 A | 9/1990 | Coggins et al. | |
| 5,052,554 A | 10/1991 | Leonard | |
| 5,067,821 A | 11/1991 | Young | |
| 5,090,597 A | 2/1992 | Johnson | |
| 5,150,706 A | 9/1992 | Cox et al. | |
| 5,201,779 A | 4/1993 | Shiao | |
| 5,222,630 A | 6/1993 | Burtis | |
| 5,277,234 A | 1/1994 | Warstler | |
| 5,366,116 A | 11/1994 | Burtis | |
| 5,500,019 A | 3/1996 | Johnson et al. | |
| 5,571,178 A * | 11/1996 | Ledergerber | A61F 2/12 623/8 |
| 5,630,843 A * | 5/1997 | Rosenberg | A61B 90/02 604/288.01 |
| 5,723,006 A * | 3/1998 | Ledergerber | A61F 2/12 600/233 |
| 5,787,944 A | 8/1998 | Sarkis et al. | |
| 6,019,776 A | 2/2000 | Preissman et al. | |
| 6,033,411 A | 3/2000 | Preissman | |
| 6,231,615 B1 | 5/2001 | Preissman | |
| 6,238,799 B1 | 5/2001 | Opolski | |
| 6,309,420 B1 | 10/2001 | Preissman | |
| 6,348,055 B1 | 2/2002 | Preissman | |
| 6,383,191 B1 | 5/2002 | Zdeblick et al. | |
| 6,520,989 B1 | 2/2003 | Eaton | |
| 6,790,238 B1 | 9/2004 | Martin | |
| 6,866,936 B2 | 3/2005 | Opolski | |
| 7,048,743 B2 | 5/2006 | Miller et al. | |
| 7,137,995 B2 | 11/2006 | Studin | |
| 7,510,579 B2 | 3/2009 | Preissman | |
| 7,645,301 B2 * | 1/2010 | Hudgins | A61F 2/441 623/17.11 |
| 7,775,716 B2 | 8/2010 | Ejeblad | |
| 8,211,173 B2 * | 7/2012 | Keller | A61F 2/12 623/7 |
| 8,555,893 B2 * | 10/2013 | Keller | A61F 2/12 128/898 |
| 8,641,758 B1 * | 2/2014 | Anderson | A61B 17/0206 623/23.64 |
| 9,023,114 B2 * | 5/2015 | Buevich | A61B 50/30 623/23.75 |
| 9,925,028 B1 * | 3/2018 | Rosenberg | A61F 2/0059 |
| 2001/0012968 A1 | 8/2001 | Preissman | |
| 2005/0267543 A1 * | 12/2005 | Heruth | A61N 1/375 607/36 |
| 2006/0184100 A1 | 8/2006 | Studin | |
| 2007/0038310 A1 | 2/2007 | Guetty | |
| 2007/0191964 A1 | 8/2007 | Preissman | |
| 2007/0276484 A1 | 11/2007 | Abell et al. | |
| 2008/0241212 A1 | 10/2008 | Moses et al. | |
| 2009/0099588 A1 | 4/2009 | Makower et al. | |
| 2010/0168808 A1 * | 7/2010 | Citron | A61L 31/10 607/5 |
| 2010/0280610 A1 | 11/2010 | Preissman | |
| 2011/0035003 A1 * | 2/2011 | Preissman | A61F 2/12 623/7 |
| 2011/0082545 A1 | 4/2011 | Freund | |
| 2011/0082546 A1 | 4/2011 | Freund | |
| 2013/0073040 A1 * | 3/2013 | Preissman | A61F 2/12 623/8 |
| 2015/0028056 A1 * | 1/2015 | Massis | A23G 3/28 222/107 |
| 2015/0032208 A1 * | 1/2015 | Preissman | A61F 2/12 623/8 |
| 2015/0126812 A1 * | 5/2015 | Anderson | A61B 17/02 600/203 |
| 2015/0238262 A1 * | 8/2015 | Buevich | A61B 50/30 604/20 |
| 2015/0272731 A1 * | 10/2015 | Racchini | A61F 2/2418 623/2.11 |
| 2016/0008171 A1 * | 1/2016 | de Juan, Jr. | A61F 9/0017 623/4.1 |
| 2016/0095697 A1 | 4/2016 | Anderson | |
| 2016/0310304 A1 * | 10/2016 | Mialhe | A61B 17/0057 |
| 2018/0116779 A1 * | 5/2018 | Marx | A61F 2/0095 |
| 2019/0107250 A1 * | 4/2019 | Rosenberg | F16N 7/12 |

FOREIGN PATENT DOCUMENTS

| | | | | |
|---|---|---|---|---|
| WO | 2010126462 A1 | | 11/2010 | |
| WO | WO-2010126462 A1 * | 11/2010 | | A61F 2/12 |
| WO | 2012177587 A1 | | 12/2012 | |

OTHER PUBLICATIONS

Examination Report in corresponding Colombian Patent Application No. NC2017/0011485 dated Feb. 23, 2018. 2 pages.
Galdiero et al. "Microbial Evaluation in Capsular Contracture of Breast Implants." Plastic and reconstructive surgery 141.1 (2018): 23-30.
No Author. "AvertPlus Surface Active Antimicrobial Coating." BioInteractions. 2016. http://www.biointeractions.com/pdfs/avertplus_overview.pdf. Retreived on Aug. 3, 2018. 1 page.
No Author. "Astute Advanced Heparin Coating." BioInteractions. 2016. http://www.biointeractions.com/pdfs/astute_overview.pdf. Retreived on Aug. 3, 2018. 1 page.
Allergan. Delivery Assistance Sleeve, Directions for Use, Jul. 12, 2011. 7 pages.
Bell et al. "An illuminating no-touch device for breast augmentation," Can J Plast Surg, vol. 17, No. 1, pp. 30-31, Spring 2009.
Supplementary European Search Report for European Patent Application No. 09844125.6 dated Jun. 9, 2012. 2 pages.
No Author. Claim Chart regarding Ledergerber 5,723,006 Feb. 28, 2012. 7 pages.
Pearne et al. Letter from Pearne & Gordon regarding Ledergerber 5,723,006 Feb. 28, 2012. 1 page.
Mladick. "No-Touch" Submascular Saline Breast Augmentation Technique, Aesth. Plast. Surg. 17:183-192, 1993.
Mladick. No-Touch Sleeve, Finesse in Breast Augmentation, 2000 Byron Medical. 1 page.

* cited by examiner

DEVICE FOR THE DELIVERY OF A PROSTHETIC IMPLANT AND METHOD OF USE THEREOF

The present application is a Continuation in Part application of pending U.S. patent application Ser. No. 15/898,537, filed Feb. 17, 2018, which is a Continuation application of issued U.S. Pat. No. 9,925,028, the disclosures of which are hereby incorporated by reference herein in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF THE INVENTION

The inventions described herein generally relate to devices to assist in the placement of prosthetic implants. The inventions further relate to a devices that hold a prosthetic implant within a structure that is (or is generally) in the shape of a conical frustum with a single opening, the interior of which is coated with one or more surface active coatings and is of suitable dimensions to hold the prosthetic implant. The application of pressure laterally along the length of the frustum ejects the prosthetic implant through the opening and into a surgical pocket that a surgeon opens in the body of a patient. Movement of the prosthetic implant out of the frustum and across the one or more surface active coatings causes interaction between the prosthetic implant and one or more surface active coatings, thereby proving the benefits that the one or more surface active coatings offer.

BACKGROUND OF THE INVENTION

Prosthetic implants, in particular breast implants, have a substantial history dating back to the first recorded implant surgery done in 1895 at the University of Heidelberg, Germany. Instead of being for cosmetic purposes, the physician (Dr. Vincent Czerny) performed the procedure by taking fat from the hip of a female for implantation into her breast, which needed reconstruction after the removal of an adenoma. Accordingly, the purpose of this first "implant" was to reconstruct a breast after devastating surgery, rather than to achieve uniform enlargement.

The first real foreign substance injected into body to achieve enlargement is perhaps the injection of paraffin, which comes in a plurality of textures and is primarily composed of petroleum jelly. Dr. Robert Gesurny, an Austrian surgeon who used the material on the testicle of a soldier in an attempt to achieve a more desirable size, first discovered the use of paraffin for boosting the size of bodily objects. Inspired by the results, Dr. Gesurny went on to use the material for breast enlargement injections, universally resulting is severely compromised outcomes.

Modern silicon gel implants, which are well known to those of ordinary skill in the art today, have a long history that dates back over the past seventy years. In fact, some evidence supports Japanese prostitutes after World War II injecting their breasts with various substances, including liquid silicon. The serious worry with silicon in liquid form was that it broke apart, forming granulomas that could then migrate basically anywhere in the body. Liquid silicone is still used, but very rarely, in microscopic amounts, and only using medical-grade silicone that is completely sterile; it remains highly controversial and is associated with serious complications. Breast implants as presently know in the art—silicon as a cohesive mass inside of a polymer "bag" structure—had their debut in the 1960s, developed by Doctor Thomas Cronin and his colleague Frank Gerow.

Although removed from the market for a number of years due to a variety of concerns and complications, silicon was allowed back into breast implants in 2006, albeit in a new form. The FDA, after years of study and experiments, finally allowed silicone gel-filled implants onto the U.S. market, which are the sole breast implant option outside of saline. Today's silicone gel is designed to feel a bit like human fat: very thick, very sticky, and classified as "semi-solid". Such technology actually represents the fifth generation of silicon implant: the first one developed by Cronin and Gerow, with various innovations, including more secure coatings, thicker gels and more natural shapes.

When any type of implant is inserted into a surgical pocket that a surgeon opens in the body of a patient, the body reacts by forming a protective lining around the prosthetic. This biological structure is referred to as the "capsule", "tissue capsule" or "scar capsule", though it should be noted that the structure it is not exactly the same as scar tissue. Although, a capsule formation is normal and happens regardless of whether the implant is smooth or textured, silicone or saline, some theorizes that problematic capsule growth is potentially attributed to manipulation of tissue during implant placement. In addition, trauma to tissue along or adjacent to the surgical pocket may suffer from the direct formation of scar tissue due to potentially over aggressive manipulation of tissue at the entry site for the implant along the edge of the surgical pocket.

Accordingly, what is needed in the art are new devices that allows for the placement of a prosthetic implant while avoiding the unnecessary manipulation of tissue adjacent to or inside a surgical pocket to minimize the development of scar tissue and the formation of any significant capsule around the prosthetic implant. What is further needed in the art are such devices with surface active coatings that minimize complications that develop during, as well as subsequent to, placement of a prosthetic implant, e.g., infection, capsular contracture, etc.

SUMMARY OF THE INVENTION

Embodiments of the invention are directed towards a surgical device for assisting in the placement of a prosthetic implant within a surgical pocket of a patient. According to one embodiment, the surgical device comprises one or more sheets of polymer shaped in the form of a conical frustum. A proximal end of the frustum is sealed and a distal end of the frustum is open, with the frustum having an elongated slit extending from the distal end toward the proximal end. Such an arrangement provides for a conical frustum having a single opening formed by the distal opening and the elongated slit, the opening configured to accept the prosthetic implant into an interior cavity of the frustum.

The elongated slit in the surgical device is sealable according to certain embodiments. According to one embodiment, a set of inter-lockable fastener elements disposed along opposing sides of the elongated slit. The set of inter-lockable fastener elements are configured to seal the elongated slit such that the distal end remains open to allow for egress of the prosthetic implant for placement into the surgical pocket. Other suitable techniques for sealing the elongated slit include, but are not limited to, adhesives, zipper, snaps, hooks and other fastening members known to those of skill in the art. The configuration of the surgical device of the present invention allows for the device to accept and place of a variety of prosthetic implant types including, but not limited to, a breast implant, a pectoral implant, a calf implant and a gluteal implant. In a given instance, the interior cavity of the frustum is sufficiently size to hold the specific type of prosthetic implant that is to be placed within the surgical pocket of the patient.

To assist transfer of the prosthetic implant from the interior of the frustum to the surgical pocket of the patient, a lubricious coating applied to the interior cavity of the frustum, allowing the prosthetic implant to easily exit the frustum. While certain embodiments utilize a water activated lubricious coating on the interior of the bag, the lubricious coating is more generally any hydrophilic gel that decreases the coefficient of friction of the inside surface of the frustum.

According to one embodiment, frustum comprises a polymer selected from the set of polymers consisting of medical grade vinyl, medical grade PVC, medical grade nylon and polyethylene. When utilizing medical grade vinyl in the construction of the fustum, various embodiments utilize medical grade vinyl that is between 0.01 inches and 0.005 inches thick. According to one embodiment, bag is composed of a polymer selected from the set of polymers consisting of medical grade vinyl, medical grade PVC, medical grade nylon and polyethylene. Various embodiments utilize one or more sheets of polymer that are between 0.01 inches and 0.005 inches thick.

In addition to the lubricious coating, one or more surface active coatings applied to the interior cavity of the frustum. Movement of the prosthetic implant across the one or more surface active coatings as it exits the frustum causes interaction between the prosthetic implant and the one or more surface active coatings. Such interaction allows the surface active coatings to provide one or more benefits that such coatings offer, such as exposure of the implant to the antimicrobial effects of a given surface active coating.

The outside of the bag may comprise a number of different markings or indicia that add the surgeon in properly placing the prosthetic implant within the surgical pocket. For example, the bag may comprise a marker, such as a circular marker, which allows the surgeon to achieve proper alignment of the prosthetic implant during placement into the surgical pocket. Application of the marker may be in accordance with any number of processes that do not affect the integrity of the material forming the bag, such as a silkscreen process. The bag may also have a plurality of size guide lines set at varying distances from the opening in at the distal end of the bag. The surgeon can use the plurality of size guide lines to properly align a cutting device to excise excess material from the distal opening of the bag.

The lubricious coating on the inside surface of the bag is activated by exposure to water, thereby resulting in a decrease in the coefficient of friction of the inside surface of the bag. Activation of the lubricious coating may be through injection of water into the interior of the bag through the use of a syringe, or aqueous submersion of the bag. Alternatively, the surgeon or technician exposes a sheet of absorbable material placed within the bag to water, thereby allowing water to wick through the absorbable material and activate a lubricious coating on an inside surface of the bag. According to one embodiment, the sheet of absorbable material changes color when exposed to water.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein;

example embodiments are provided merely to be illustrative. Those of skill in the art understand that other embodiments may be utilized and structural changes may be made without departing from the scope of the present invention. Likewise, a reasonably broad scope for claimed or covered subject matter is intended. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Figure 1:
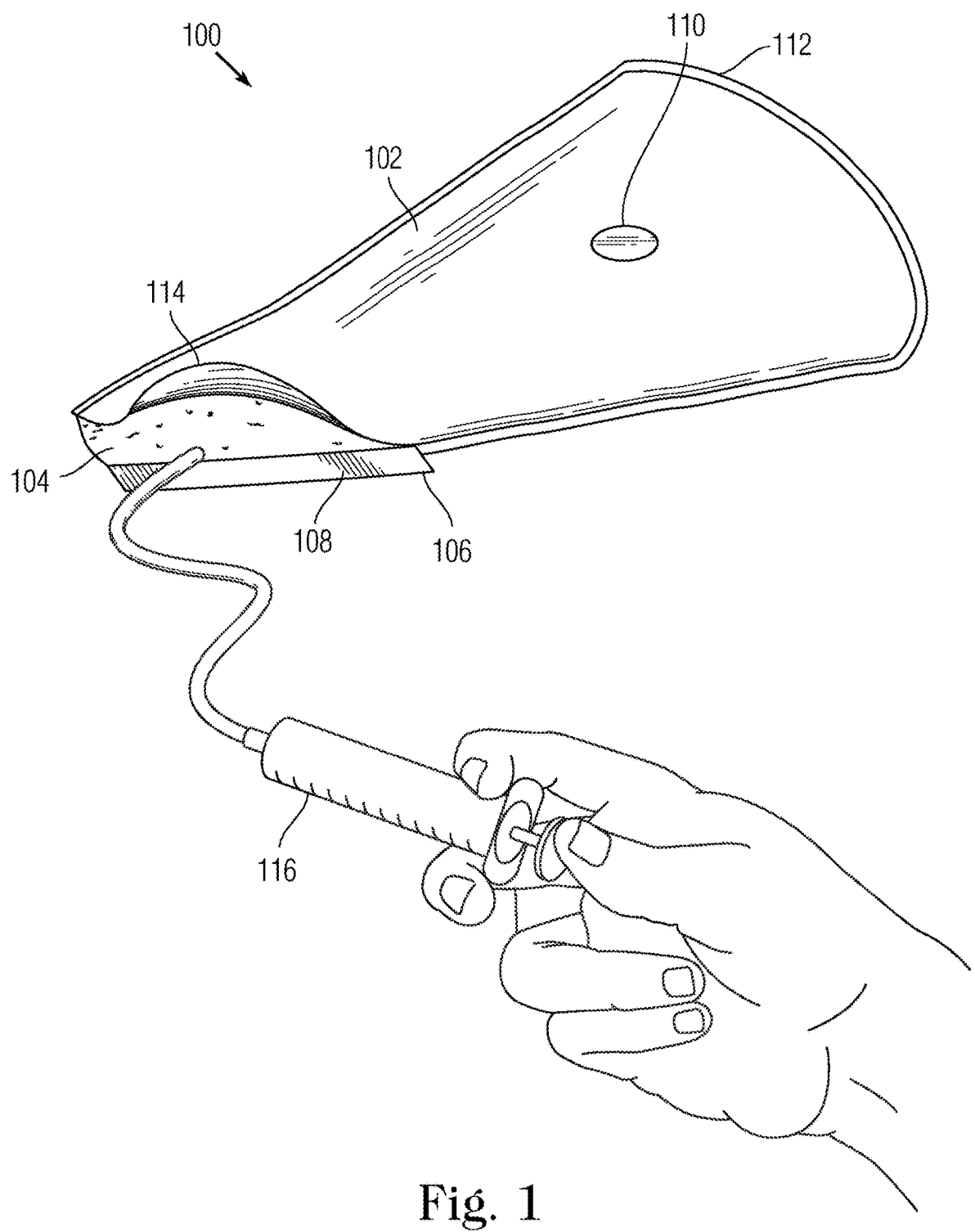
FIG. 1 illustrates a top perspective view of a surgical device for assisting in the placement of a prosthetic implant within a surgical pocket of a patient according to one embodiment of the present invention.

FIG. 1 illustrates a top perspective view of a surgical device 100 for assisting in the placement of a prosthetic implant within a surgical pocket of a patient according to one embodiment of the present invention. The surgical device 100 comprises a bag shaped as a conical frustum in which a proximal end 112 of the conical frustum is sealed and a distal end of the conical frustum is open 104 with an elongated slit 114 extending from the distal end towards the proximal end 112. According to one embodiment, the proximal end of the bag 100 is sealed with an RF weld. The bag 100 may be formed from a single sheet of material that is stamped or cut using a die or other suitable technique and folded around itself, or may be formed by multiple panels, e.g., front and back panels, that are joined together.

The opening 104 formed by the distal opening and the elongated slit 114 is of sufficiently large size to accept a prosthetic implant into the bag. Accordingly, manufacture of the surgical device 100 may comprise production of the surgical device in various sizes or volumes to accommodate prosthetic implants of various sizes. For example, the surgical device 100 may be sized differently to accommodate a gluteal implant as opposed to a breast or calf implant. According to one embodiment, the bag is of sufficient capacity to seat the prosthetic implant and activate the adhesive to allow the elongated slit to be sealed with the bag horizontal relative to a standing surgeon.

A technician preparing the surgical device 100 for use on a patient places the implant within the device and seals the elongated slit such that the distal end remains open to allow for egress of the implant from the bag and placement into the surgical pocket. According to the embodiment of FIG. 1, a flap 106 is formed along one side of the elongated slit 114 such that a technician can fold the flap 106 over the elongated slit 114 to form the seal. An adhesive 108 or other fastening member may be affixed along a portion of the elongated slit (which may be on the flap if present) form a seal such that the distal end remains open to allow for egress of the implant from the bag for placement into the surgical pocket. Advantageously, a ridge formed by the sealed elongated slit provides a support guide for the prosthetic implant during placement into the surgical pocket.

The inside surface of the surgical device 100, which is a bag in the form of a conical frustum, is treated with a lubricious coating. Lubricity is a property that describes how slippery a surface is, more specifically, the value of its coefficient of friction. Embodiments of the present invention benefit from this type of slippery surface treatment because it reduces the insertion force that the surgeon must apply to propel or eject the prosthetic implant through the distal opening in the bag, avoiding possible puncture damage to the prosthetic implant and severe abrasion between the implant surface and the interior surface of the bag.

The lubricious coating can be applied to interior surface of the bag 100 in a number of ways. One application technique is dip coating, which entails suspending the bag from a support, lowering it into a liquid coating solution and then withdrawing. The coating sticks to the surface as the support draws the bag up and out of the solution. An alternative is spray coating, which is akin to airbrushing and involves spraying a nebulized mist over the interior surface of the bag. Film coating is another type of application process in which long rolls of material that form the bag are drawn from reel to reel through a tank of liquid coating. Other processes for the application of the lubricious coating include chemical vapor deposition and silk screening, which is primarily suitable when working with flat surfaces, such as the raw material that forms the bag.

Any of the above-described coating techniques involves a drying or curing process to permanently affix the lubricious coating to the interior surface of the bag. Two prevalent methods for curing hydrophilic coatings are heat and ultraviolet ("UV") light. When utilizing heat-cured coatings, the bag is placed within an oven for a given period of time. Such controlled heating accelerates drying of the coating and any necessary chemical reactions taking place within the coating (or between the coating and the bag), such as crosslinking, which allow the coating to stick to the interior surface of the bag, as well as provide durability. For embodiments that utilize lubricious coatings that use UV light for the curing step, the interior surface of the bag is exposed to UV light for a given period of time, which has the effect of stimulating any necessary chemical reactions for curing. Completion of the curing process affixes the lubricious coating to the interior surface of the bag.

The lubricious coating is hydrophilic. Hydrophilic coatings exhibit so-called "water loving" characteristics. From a chemical perspective, these coatings participate in dynamic hydrogen bonding with surrounding water. In some cases, hydrophilic coatings are also ionic, and may further exhibit negative charge, which facilitates additional aqueous interactions. Physically, these chemical interactions with water give rise to hydrogel materials that may exhibit extremely low coefficients of friction. Taken together, these chemical and physical characteristics describe a class of materials that are wettable, lubricious, and suitable for tailored biological interactions.

In addition to the application of a lubricious coating to interior surface of the bag 100, a number of disparate surface active coatings may also be applied to the interior surface of the bag 100. The use of surface active coatings on the interior surface of the bag 100 has advantages over drug eluting covers or coatings that may be applied to the surface of a medical device. One advantage of such surface active coatings over drug eluting coatings is that the surface active coatings do not elute or otherwise release from the interior surface of the bag, but rather remain bonded to the interior surface. A further distinction over the use of drug eluting compounds is that the mechanism of action for such surface active coatings is not a specific antibiotic that is targeted towards a specific genus and species of bacteria, but rather a broad based antimicrobial action based on cell membrane rupture of a given virus, bacteria, protozoa, microbe, etc.

According to one embodiment, a given one of the one or more surface active coatings is applied by dipping the bag, where the surface active coating is in a liquid phase, in a volume of the given surface active coating. Accordingly the surface active coating may be simultaneously applied to one or more surfaces of the bag. Similarly, where the surface active coating is in liquid form, the surface active coating may be applied to a surface of the bag by spraying or airbrushing the surface active coating onto the desired surface. Likewise, vapor depositing and other coating techniques know to those of skill in the art may be used to apply the surface active coating to one or more surfaces of the bag. It should also be noted that multiple surface active coatings can be combined in solution for simultaneous application to the desired surfaces.

As with the discussion herein regarding certain lubricious coatings, the surface active coating is cured, if required, which may be by heat, UV, etc., depending on the curing requirements of the specific surface active coatings. According to one embodiment, components of a first surface active coating are bonded to components of another surface active coating, which is itself then bonded to the surface of the bag, both of which may comprise bonding by way of a curing process. Curing allows for bonding of the one or more surface active coatings to bind to the bag, which may be ionic or covalent bonds, or combinations thereof, again depending on the specific surface active coatings applied to the surface of the bag, as well as any interactions therebetween.

As the prosthetic implant moves through the interior of the bag towards the egress point at the distal end, the surfaces of the prosthetic implant come into communication with the surface active coatings, which then interact with any foreign agents on the exterior surface of the prosthetic implant prior to placement in the surgical pocket. Such communication between the prosthetic implant and the one or more surface active coating allows the coatings to impart one or more benefits that such coatings offer. For example, where the surface active coating has an antimicrobial component, the surface of the prosthetic implant receives the antimicrobial benefits of the surface active coating without any medication or drugs unnecessarily or undesirably eluting into the body of the patient.

Figure 9:
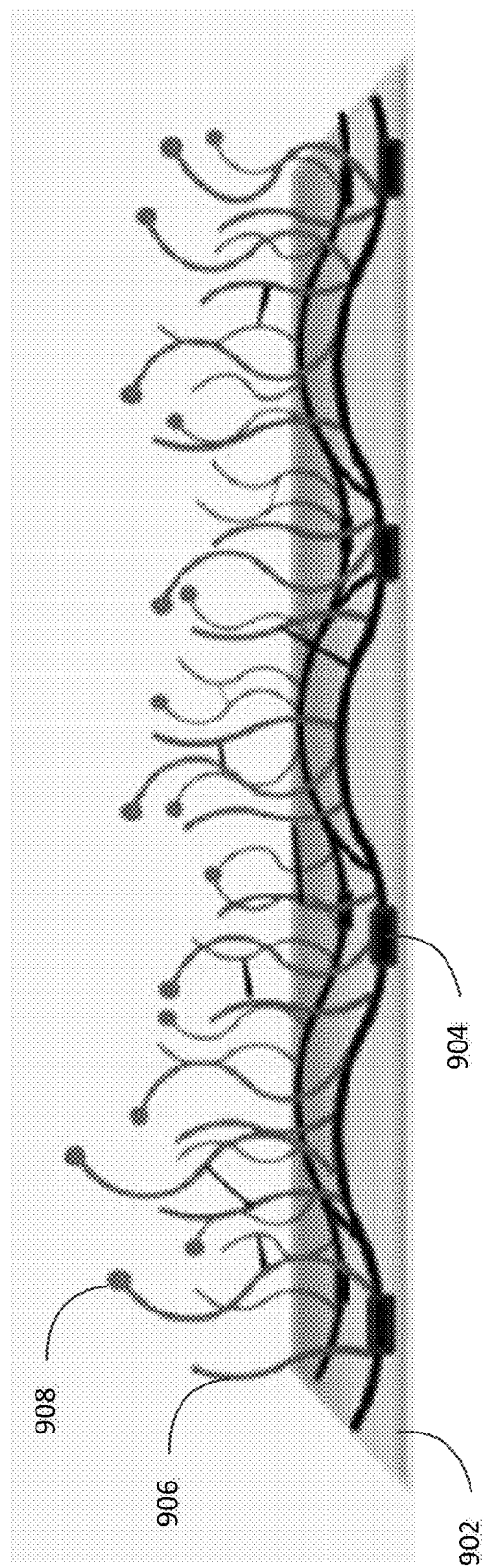
FIG. 9 illustrates one or more surface active coatings that are bonded to an interior surface of a surgical device for assisting in the placement of the prosthetic implant.

The application of such surface active coatings is an advantageous improvement in the functioning of the surgical device in placing a prosthetic implant due to its ability to reduce the occurrence of infection and other complications that arise during and after placement. The issue involves the adhesion of bacteria onto an implantable medical device, such as a prosthetic implant. Adsorption of protein on the outer surface of the implantable device provides a suitable location for bacterial adhesion. Bacterial adhesion on the exterior surface of the prosthetic implant, even in minor amounts, has the possibility of leading to bacterial division, secretion and, ultimately, the development of biofilm across the surface of the prosthetic implant subsequent to its placement inside the patient. Again, the application of surface active coatings to the interior of the bag allows the surfaces of the prosthetic implant come into communication with the surface active coatings. This communication allows for the one or more surface active coatings to interact with any foreign agents on the exterior surface of the prosthetic implant prior to placement in the surgical pocket FIG. 9 illustrates one exemplary surface active coating for application to the interior surface of the bag. In the exemplary illustration of FIG. 9, the interior surface of the bag 902 has affixed thereto a coating that comprises a non-thrombogenic component 906 and an antimicrobial component 908. Each of the non-thrombogenic components 906 and antimicrobial components 908 are bonded to a polymer backbone 904 that is further bonded to the interior surface of the bag 902. One exemplary surface active coating that can be bonded to the interior surface of the bag to provide such non-thrombogenic and antimicrobial effects is the AdvertPlus™ surface active antimicrobial coating available from BioInteractions Ltd.

Turning back to FIG. 1, a technician may hydrate the interior of the bag 100 to activate the lubricious coating by injecting water into the bag through the use of a syringe 116. Alternatively, or in conjunction with the foregoing, the technician may hydrate a polymer insert (not pictured) placed within the interior of the bag 100. When hydrating the polymer insert, the insert serves to wick the fluid throughout the interior of the bag, thereby activating the lubricious coating. The polymer insert is preferably sized to follow the contours of the interior of the bag 100 and may comprise any material that suitably wicks fluid throughout its surface including, but not limited to Lightweight Stabilizer (60% polyester/40% Rayon), Medium Weight Stabilizer (60% polyester/40% Rayon) and medium to heavyweight sew-in interfacing (100% Polyester).

Different markings on the exterior of the bag 100 assist the technician in preparing the bag for implant delivery and the surgeon in the delivery process. For example, a marker 110 on the outside of the bag allows the technician to align the prosthetic implant properly in the bag 100, such as by aligning the marker with a physical marker on the bottom of the implant. In this manner, the surgeon is aware of the bottom position of the implant upon delivery and can ensure that the implant is not delivered into the surgical pocket bottom side up. Application of the marker to the bag is in accordance with any process that permanently deposits the marker on the outer surface of the bag without harming or otherwise causing any degradation to the bag itself, e.g., through a silkscreen process, inkjet printing or hand application with suitable pens or markers. The exterior of the bag 100 may further comprise a plurality of size guide lines to properly align a cutting device when excising material from the distal opening of the bag. Excising material from the distal opening of the bag allows the technician to increase the aperture diameter of the distal opening, thereby allowing the device to accommodate larger implant sizes without causing damage to the opening 104 at the distal end of the bag 100.

Figure 2A:
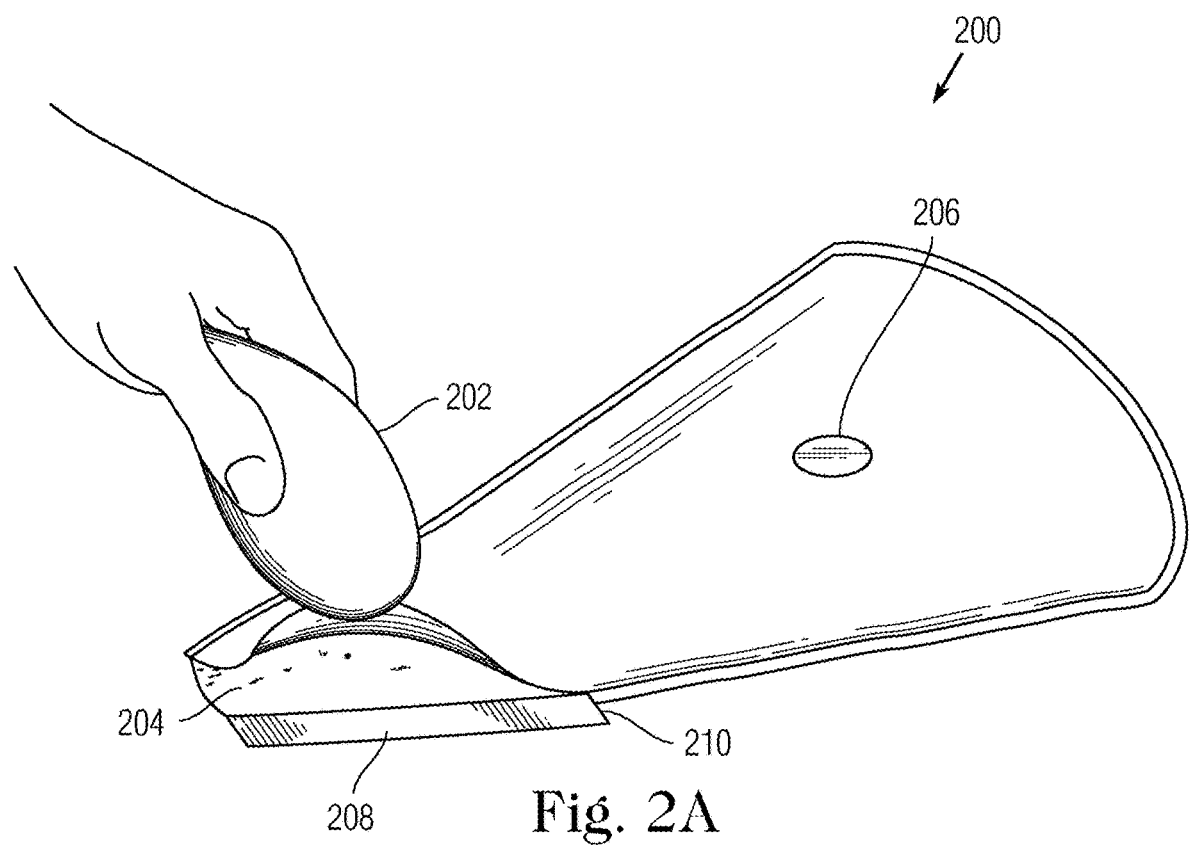
FIG. 2A illustrates a top perspective view of a surgical device for assisting in the placement of a prosthetic implant within a surgical pocket of a patient in conjunction with a prosthetic implant according to one embodiment of the present invention.
Figure 2B:
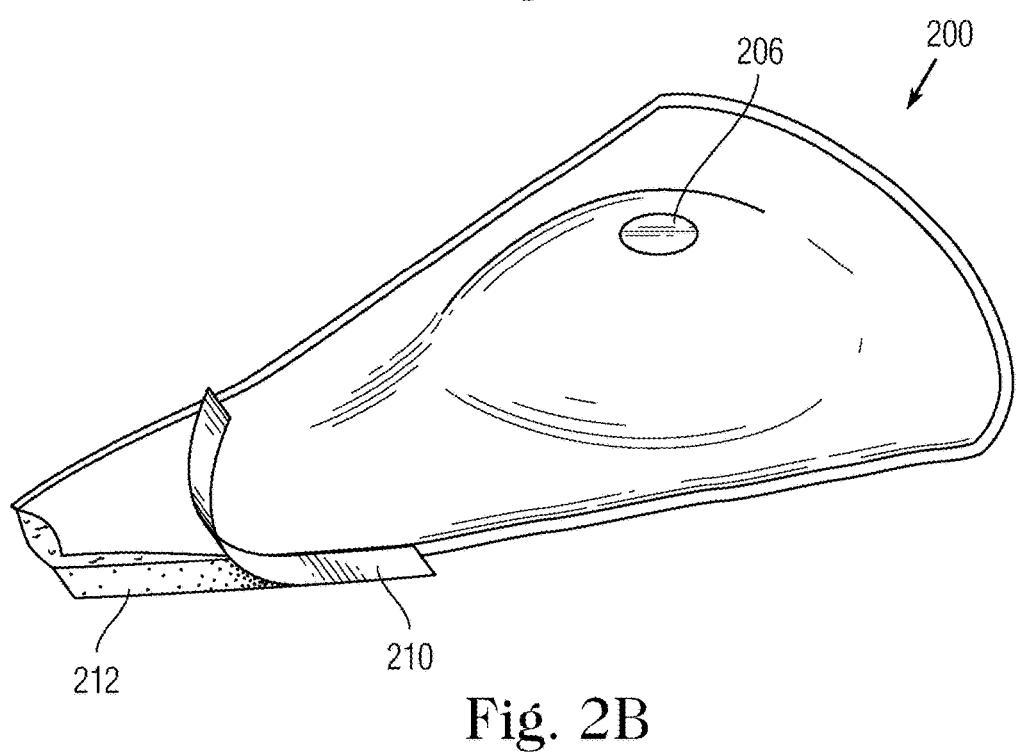
FIG. 2B illustrates the surgical device of FIG. 2A with an implant seated with the surgical device and a partially exposed adhesive strip according to one embodiment of the present invention.
Figure 2C:
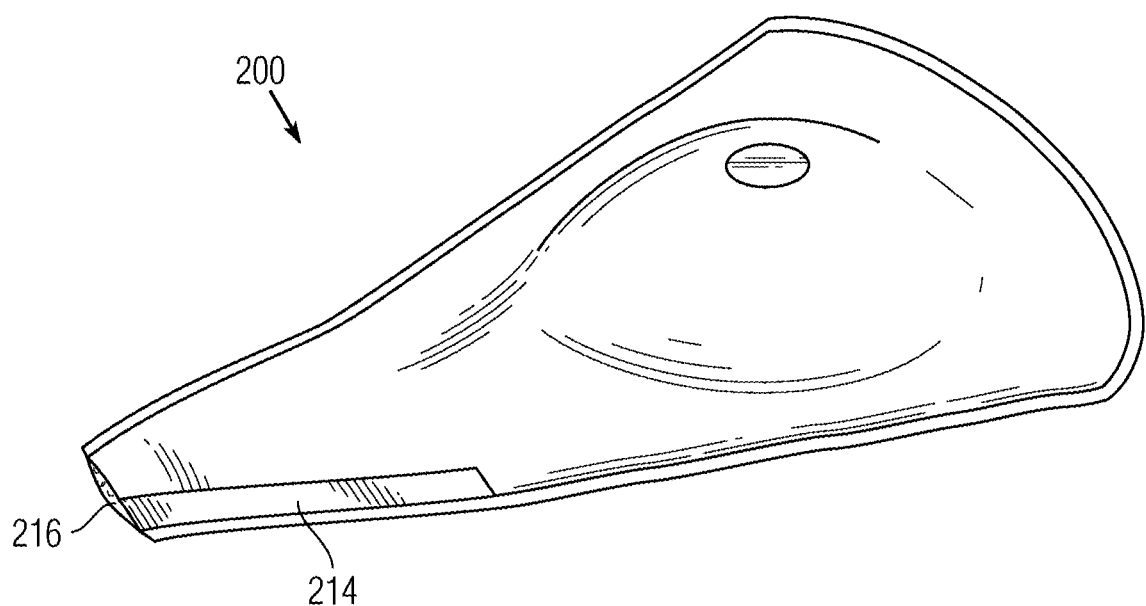
FIG. 2C illustrates the surgical device of FIG. 2A with the elongated slit sealed such that the distal end remains open to allow for egress of the implant from the bag for placement into the surgical pocket according to one embodiment of the present invention.

FIGS. 2A-2C illustrate placement of an implant into and the sealing of a surgical device for assisting in the placement of the prosthetic implant within a surgical pocket of a patient. Turning to FIG. 2A, the bag 200 is set out to allow for loading of the prosthetic implant 202 into the interior of the bag 200. The distal opening 204 and elongated slit are sized to accommodate placement of the prosthetic implant 202 into the bag 200 and further align a marker on the implant with the marker on the bag 200, thereby providing the surgeon with an indication as to the orientation of the implant within the bag. According to the embodiment that FIGS. 2A-2C illustrate, a flap 208 is formed along one side of the elongated slit and covered by an adhesive backing 210 that covers an underlying adhesive until such a time as when the technician is ready to seal the elongated slit.

Continuing with FIG. 2B, the implant 202 is seated within the interior of the bag 200. Advantageously, the technician aligns a physical marker on the implant with the marker on the outside of the bag. Accordingly, the surgeon has an indication as to the orientation of the implant 202 within the bag and can maintain such orientation for the duration of the implant's movement through the bag and into a surgical pocket that the surgeon prepares to accept the implant. The technician seals the elongated slit, thereby maintaining the opening in the distal end of the bag, which the technician may further trim to increase the aperture of the opening when placing implants of various sizes. According to the present embodiment, an adhesive is applied to a flap that runs along one edge of the elongated slit.

The technician removes an adhesive backing 210 to expose an underlying adhesive 212 that seals the elongated slit by adhesing the flap to the exterior surface of the bag. FIG. 2C illustrates the surgical device with the elongated slit sealed such that the distal end 216 remains open to allow for egress of the implant 202 from the bag 200 for placement into the surgical pocket. As can be seen, the flap 214 is folded over and adhesed to the outside surface of the bag 200, leaving the distal opening 216 for placement in the surgical pocket during delivery of the implant 202.

Figure 3:
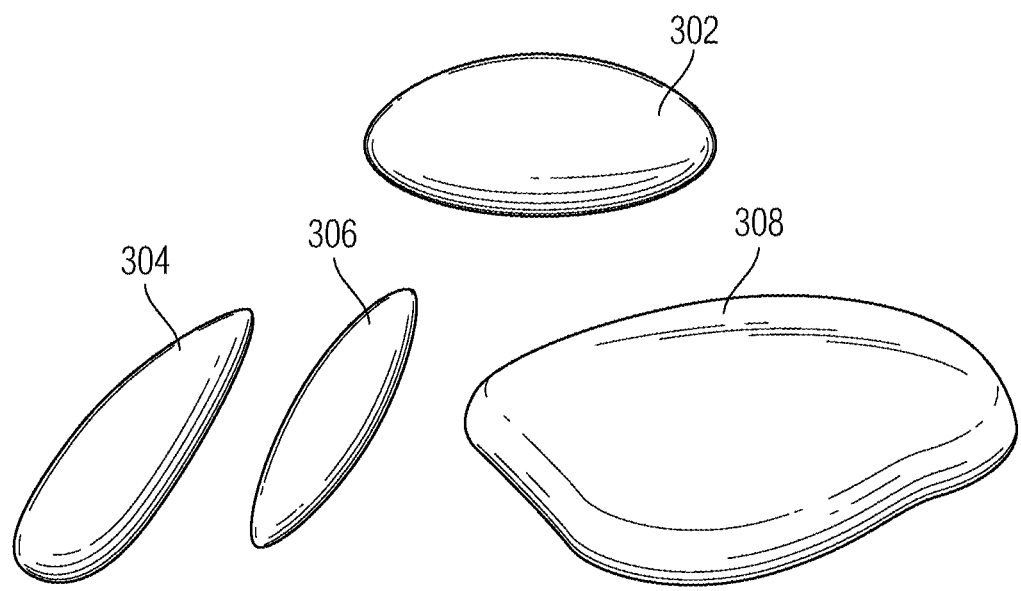
FIG. 3 illustrates several exemplary prior art prosthetic implants.

FIG. 3 presents a number of prior art implants that are suitable for use with embodiments of the present invention. For example, breast 302, gluteal 308 and various calf implants 304 and 306, may be set or otherwise placed through use of various embodiments. Those of skill in the art recognize that certain aspects of the bag geometry might require slight modification from the illustrations presented in conjunction with the embodiments depicted herein. By way of example and not limitation, when placing a gluteal implant 308, which is typically of a larger volume than a breast implant 302, the length of the bag, as well as possibly the angle at which the distal opening forms, may require commensurate increases.

Figure 4A:
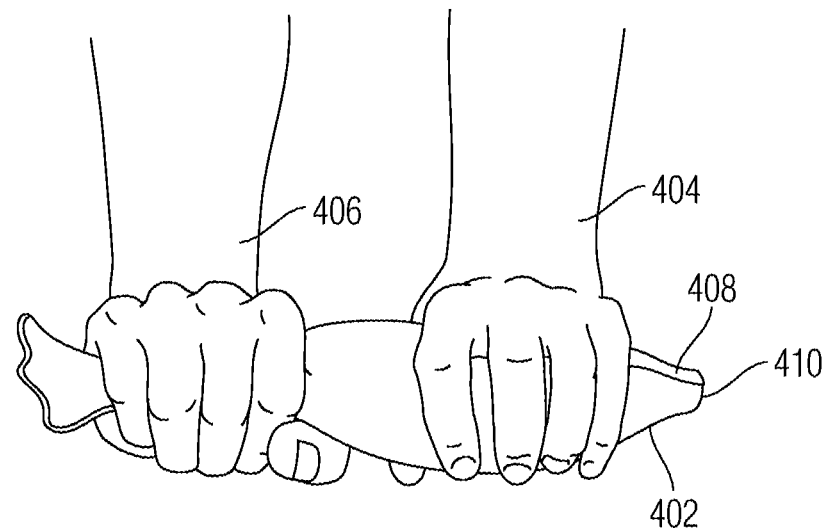
FIGS. 4A and 4B illustrate manipulation of a prosthetic implant through a surgical device for assisting in the placement of the prosthetic implant within a surgical pocket of a patient according to one embodiment of the present invention.
Figure 4B:
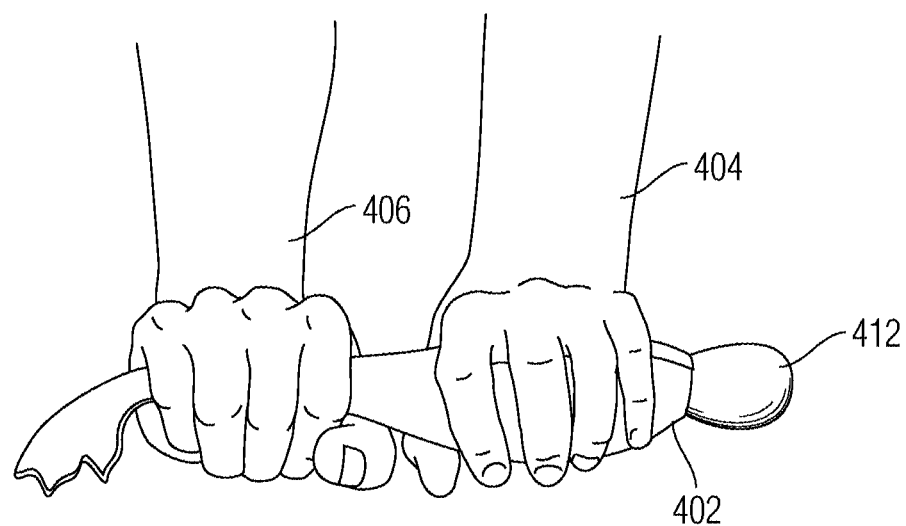

As FIGS. 4A and 4B illustrate, the implant is set within the bag 402 and the elongated slit 408 sealed such that sequential application of pressure by the hands 404 and 406 of the physician serve to manipulate the implant 412 out through the opening 410 in the distal end of the bag 402. As described above and further herein in connection with various embodiments of the invention, the implant is set and can further be aligned with a marker on the bag to understand alignment of the implant as the surgeon manipulates the implant along the length of the bag 402. FIGS. 4A and 4B illustration the application of a twisting motion or the sequential application of pressure laterally along the bag by the hands of the surgeon 404 and 406, typically with the proximate hand 406 applying pressure while the distal hand 404 provides support, although other hand and pressure application configurations fall within the scope of the invention. The application of pressure as such serves to drive the implant out the distal opening 410 and into a surgical pocket that the surgeon has prepared to accept the implant.

Figure 5A:
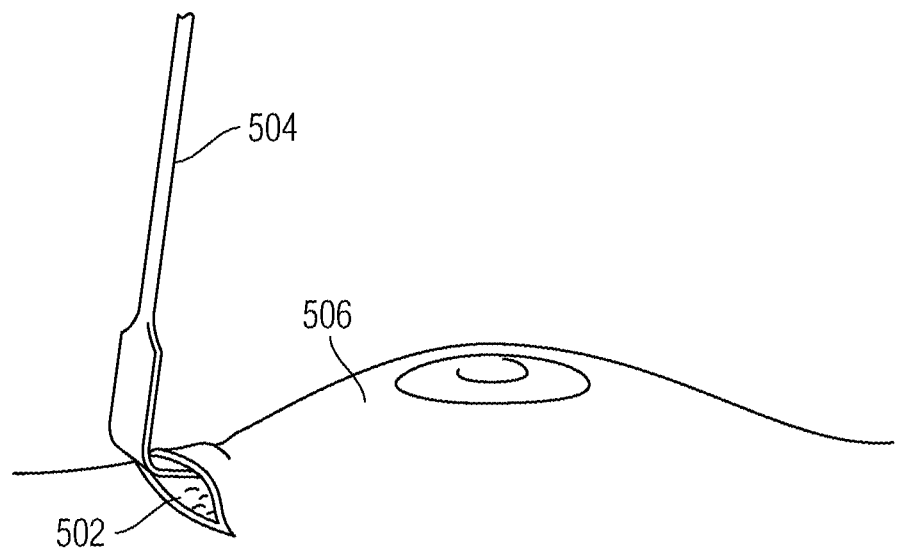
FIGS. 5A and 5B illustrate placement of a prosthetic implant through a surgical device for assisting in the placement of the prosthetic implant within a surgical pocket of a patient according to one embodiment of the present invention.
Figure 5B:
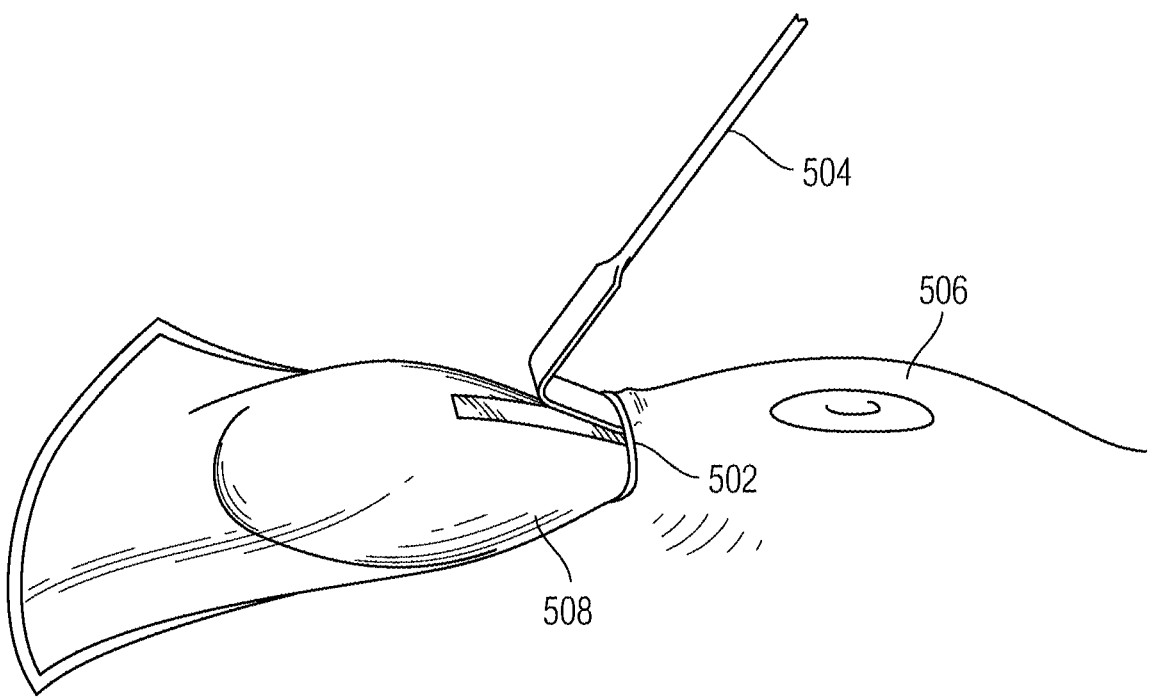

FIGS. 5A and 5B continue the process illustrated by FIGS. 4A and 4B in which the implant is set into a surgical pocket 502 in the body 506 of a patient. The surgeon or a technician can utilize a surgical retractor 504 to manipulate the surgical pocket 502 and properly position the surgical pocket to receive the implant. For example, a technician utilizes the surgical retractor 504 to hold open the surgical pocket 502 that the surgeon incises in the body 506 of the patient, such as under the breast. The surgeon, using the implant set in the bag with the elongated slit sealed 508, introduces the distal end of the bag into the open surgical pocket 502. Because activated lubricious coating on the interior of the bag greatly reduces the coefficient of friction on the interior surface of the bag, manipulation by the surgeon allows the implant to be easily driven into the surgical pocket 502 with little disruption or unnecessary trauma to the surgical pocket 502 or surrounding tissues. Once the surgeon sets the implant into the surgical pocket, he or she removes the bag 508 and the wound is closed through the application of sutures, staples, glue or other techniques known to those of skill in the art suitable to close the surgical pocket.

As described above, Embodiments of the invention may utilize various techniques for affixing the edges of the elongated slit to seal the elongated slit such that the distal end of the bag remains open to allow for egress of the implant from the bag. Although above-described embodiments illustrate the use of adhesives, other structures such re-closable fasteners or other adhesion or fastening techniques known to those of skill in the art may readily be utilized with the device.

Figure 6A:
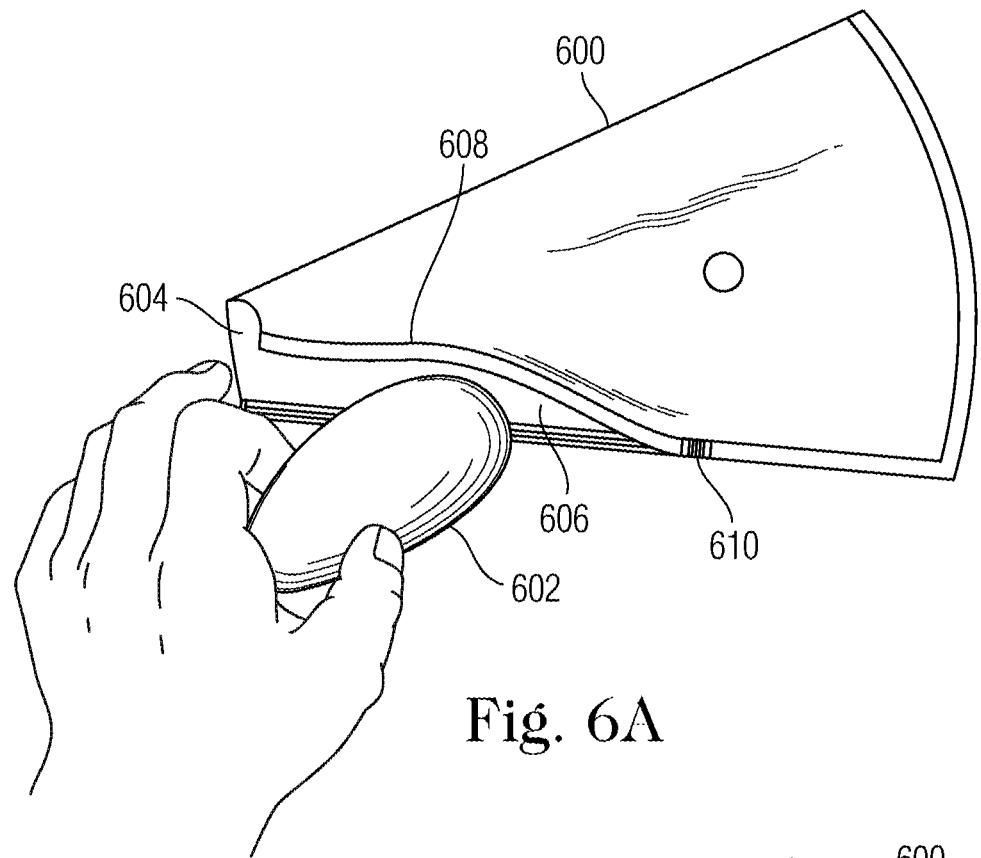
FIGS. 6A-6C illustrate a surgical device for assisting in the placement of the prosthetic implant within a surgical pocket that utilizes inter-lockable fastener elements in a first configuration on a pair fastener strips on each side of an elongated slit according to a one embodiment of the invention.
Figure 6B:
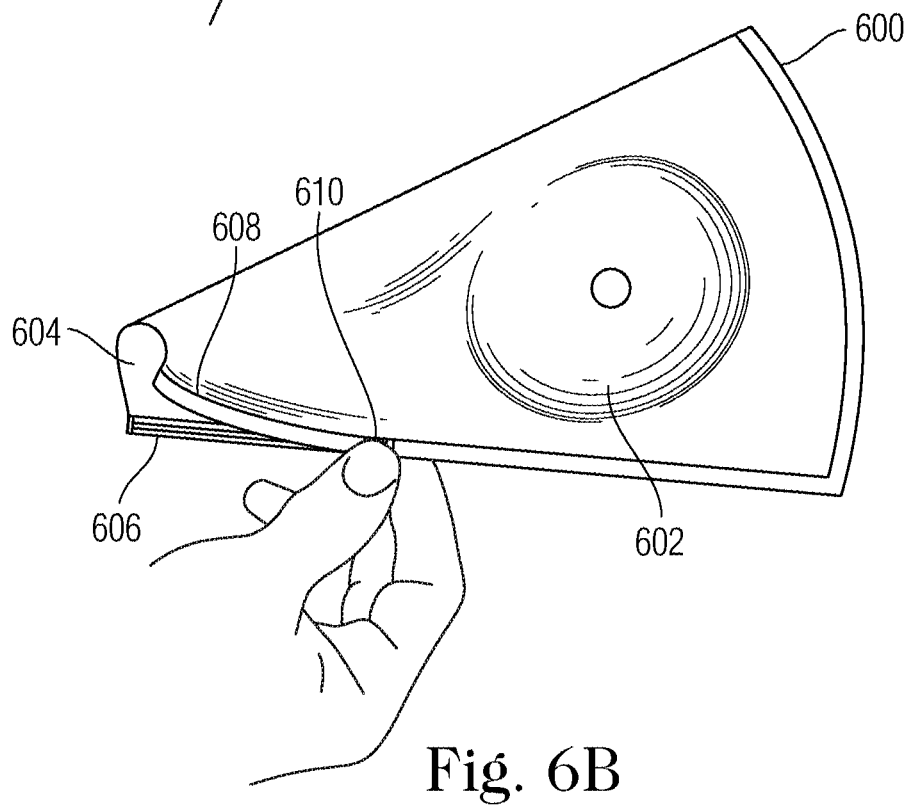
Figure 6C:
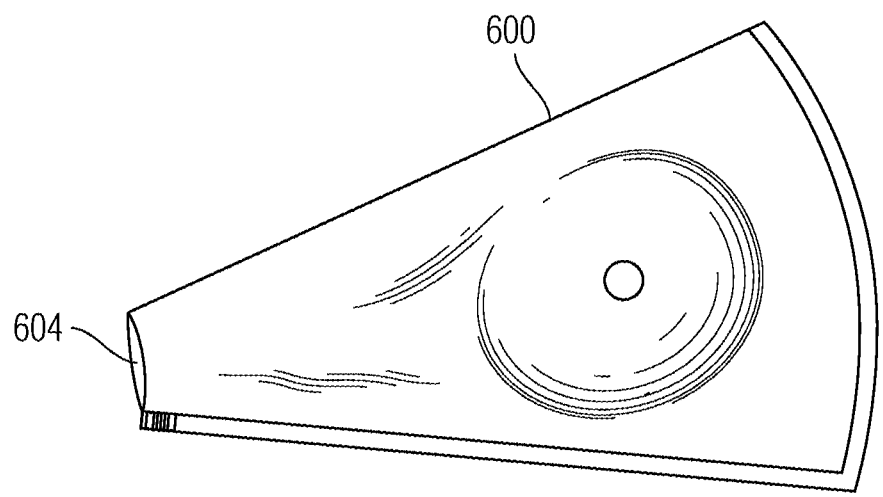

FIGS. 6A-6C illustrate a surgical device for assisting in the placement of the prosthetic implant within a surgical pocket that utilizes inter-lockable fastener elements in a first configuration on a pair fastener strips on each side of an elongated slit according to a one embodiment of the invention. More specifically, FIGS. 6A-6C present the progression of setting a breast implant into the delivery bag, which comprises a set of inter-lockable re-closable fasteners and a slider along the edges of the elongated slit such that the elongated slit seals through fastening of the inter-lockable re-closable fasteners. The inter-lockable re-closable fasteners can also be closed by hand through alignment and application of pressure along the same.

Starting with FIG. 6A, the bag 600 is in an "open" configuration in which the elongated slit, which comprises a set of inter-lockable re-closable fasteners 606 and 608, and distal opening allow for insertion of a prosthetic implant 602 into the bag. In the embodiment that FIG. 6A illustrates, the prosthetic implant 602 is a breast implant. A slider 610, located at the end of the elongated slit closet to the proximal end of the bag, allows for roll-off closure of the set of inter-lockable re-closable fasteners. Turning to FIG. 6B, the technician places the implant 602 into the interior of the bag 600 and begins to roll off the slider 610 along the set of inter-lockable re-closable fasteners 606 and 608 in the direction of the distal opening 604. Finally, transitioning to FIG. 6C, the set of inter-lockable re-closable fasteners are locked, thereby sealing the elongated flap such that the distal end remains open to allow for egress of the implant from the bag for placement into the surgical pocket. Although FIG. 6C illustrates the slider 610 remaining in place at the distal opening of the bag 600, the slider can also be run off the end of the bag 600 and discarded as the elongated slit is sealed with the implant 602 in place and ready for delivery.

Figure 7A:
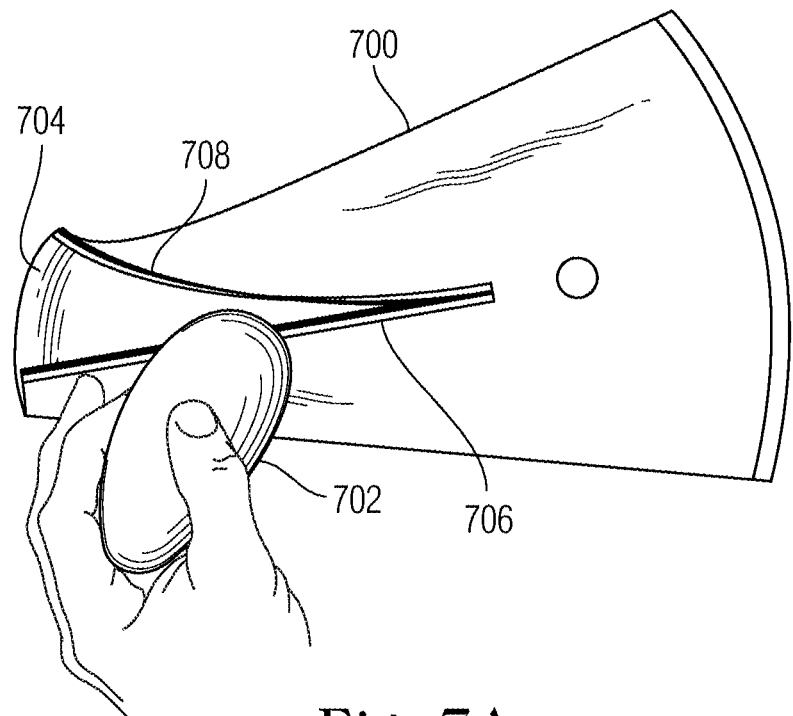
FIGS. 7A-7C illustrate a surgical device for assisting in the placement of the prosthetic implant within a surgical pocket that utilizes inter-lockable fastener elements in a second configuration on a pair fastener strips on each side of an elongated slit according to a one embodiment of the invention.
Figure 7B:
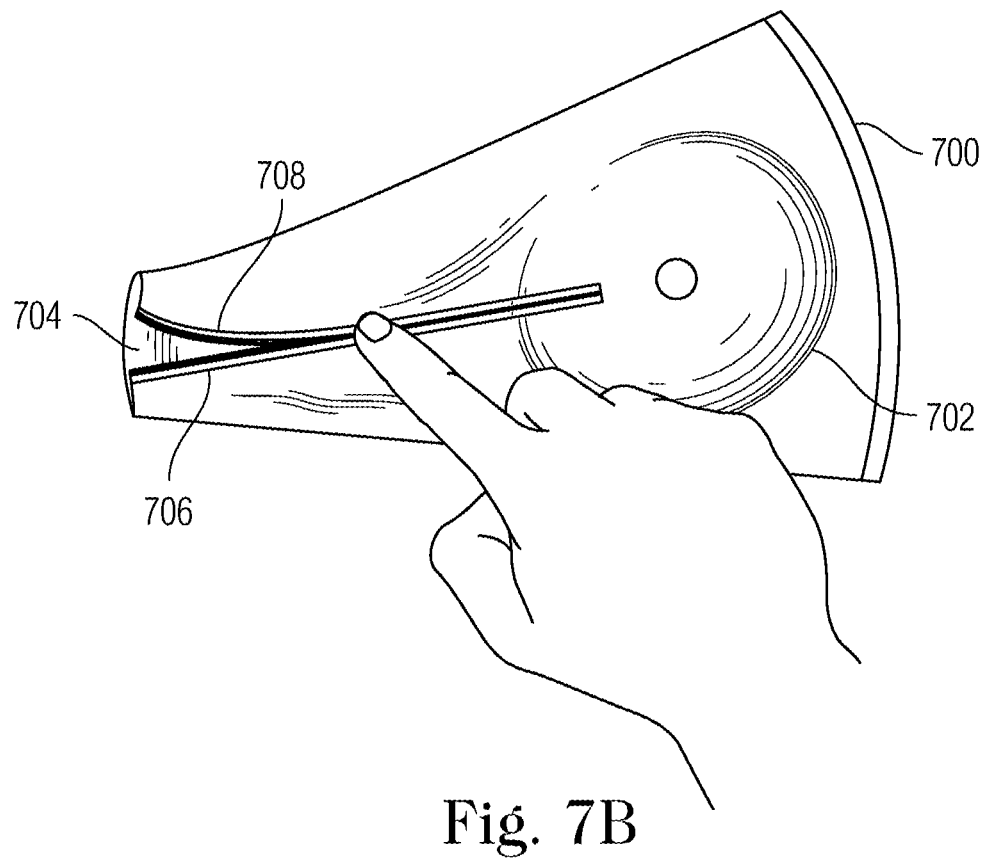
Figure 7C:
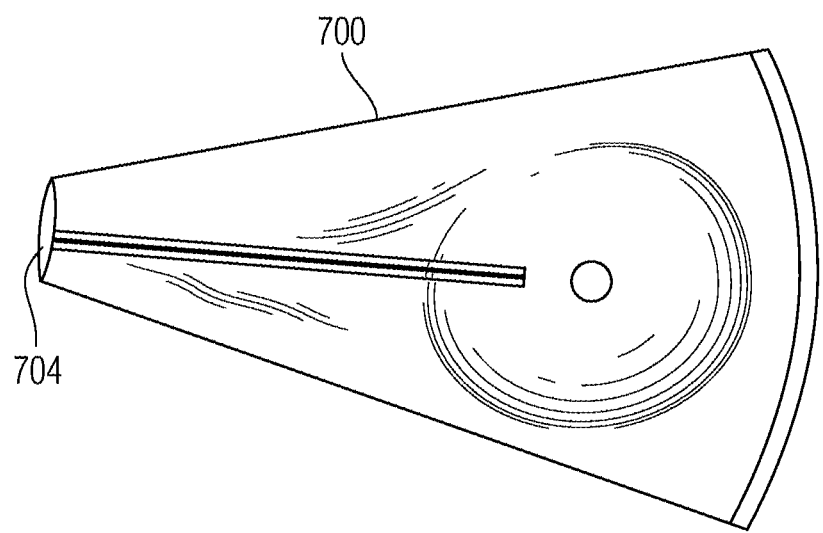

FIGS. 7A-7C illustrate a surgical device for assisting in the placement of the prosthetic implant within a surgical pocket that utilizes inter-lockable fastener elements in a second configuration on a pair fastener strips on each side of an elongated slit according to a one embodiment of the invention. More specifically, FIGS. 7A-7C present the progression of setting a breast implant into the delivery bag, which comprises a set of inter-lockable re-closable fasteners and a slider along the edges of the elongated slit such that the elongated slit seals through fastening of the inter-lockable re-closable fasteners and lie flat in relation to the surface of the bag.

Starting with FIG. 7A, the bag 700 is in an "open" configuration in which the elongated slit and distal opening allow for insertion of a prosthetic implant 702 into the bag. The elongated slit comprises a set of inter-lockable re-closable fasteners 706 and 708 that lie flat in relation to the surface of the bag. In the embodiment that FIG. 7A illustrates, the prosthetic implant 702 is a breast implant. Turning to FIG. 7B, the technician places the implant 702 into the interior of the bag 700 and begins to apply pressure to the set of inter-lockable re-closable fasteners 706 and 708 in the direction of the distal opening 704. Transitioning to FIG. 6C, the technician locks the set of inter-lockable re-closable fasteners, thereby sealing the elongated flap such that the distal end remains open to allow for egress of the implant from the bag for placement into the surgical pocket. According to the embodiment of FIG. 7A-7C, the set of inter-lockable re-closable fasteners are arranged such that the fasteners lie flat in relation to the surface of the bag, although those of skill in the art recognize that other configurations are suitable.

Figure 8:
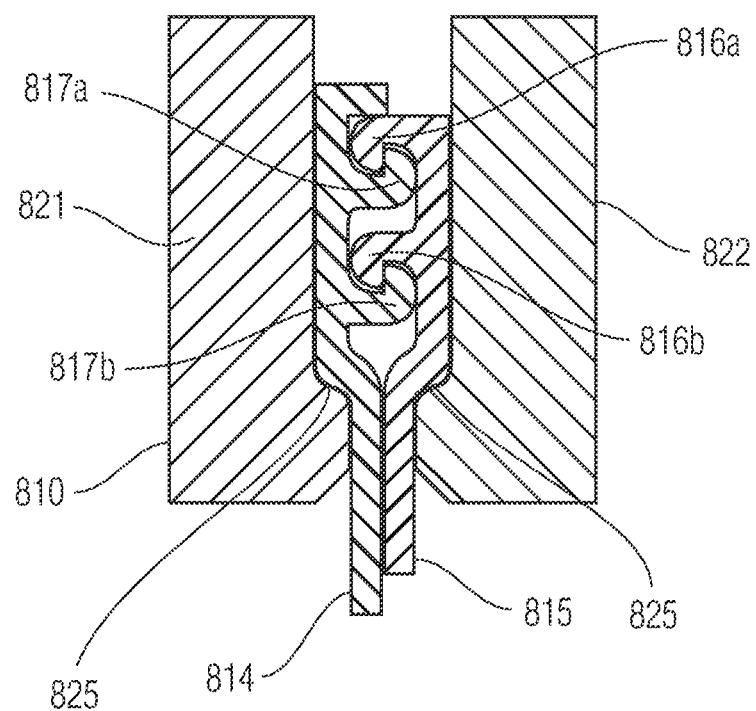
FIG. 8 illustrates a cross-sectional view of inter-lockable fastener elements positioned along the edges of the elongated slit and a locking slider in accordance with one embodiment of the present invention.

FIG. 8 presents a detailed cross-sectional view of one embodiment of the invention in which inter-lockable re-closable fasteners and a slider provide a mechanism for sealing the elongated slit. The elongated slit in the bag comprises a pair of opposing flexible sides 812 and 813. The side 812 has a top edge having a first fastener strip 814 attached thereto. According to one embodiment, the first fastener strip 814 has an inner surface on the inside of the bag and an outer surface on the outside of the bag. The side 813 has a top edge having a second fastener strip 815 attached thereto. The second fastener strip 815 in certain embodiments has an inner surface on the inside of the bag and an outer surface on the outside of the bag. The strips 814 and 815 may be extruded separately for attaching to the respective sides of the bag. Alternatively, the strips 814 and 815 may be extruded integrally with the sides of the bag, e.g., along the sides forming the elongated slit.

Each fastener strip may utilize one or more closure elements, but the number of closure elements on opposing strips must be equal or otherwise balanced. In accordance with the embodiment of FIG. 8, the first fastener strip has an uppermost closure element 816*a* and a bottommost closure element 816*b*. The closure elements 816*a* and 816*b* project laterally from the inner surface of fastener strip 814. Likewise, the second fastener strip 817 has at least an uppermost closure element 817*a* and a bottommost closure element 817*b*. The closure elements 817*a* and 817*b* project laterally from the inner surface of fastener strip 815. When the bag is closed, the closure elements of the first fastener strip interlock with the corresponding closure elements of the second fastener strip.

When the bag is open, the first and second fastener strips 814 and 815 are separated from each other on the respective sides. Closure elements 816*a*, 817*a*, 816*b*, and 817*b* have a complimentary cross-sectional shape that achieves closure by pressing the fastener strips together. The slider 810 accomplishes the pressing action through actuation, which straddles the fastener strips 814 and 815 and is adapted to close or open the closure elements 816 and 817 of the re-closable fastener. The slider 810 moves between a closed position and an open position. Thus, when the slider 810 reaches the closed position at distal end of the bag, the bag is closed and the closure elements interlock throughout a portion of the length of the elongated slit. When the slider reaches the open position at the end of the elongated slit closest to the proximal end of the bag, the bag is open and the closure elements are disengaged throughout substantially the entire length of the elongated slit. Those of skill in the art recognize that it is sufficient for at least the bottommost closure elements to interlock with each other throughout substantially their entire length in order for the elongated slit to be closed. Preferably, although not necessarily, the uppermost closure elements also interlock with each other.

As indicated, the slider is operative to interlock the closure elements of the fastener strip on each side of the elongated slit. As FIG. 8 illustrates, the slider 810 comprises an inverted U-shaped member having a top 820 for moving along the top edges of the fastener strips 814 and 815. The slider 810 has sidewalls 821 and 822 depending from the top 820. Sidewalls 821 and 822 extend downward along the outer surface of the fastener strips 814 and 815, to a point at or below the closure elements 816 and 817, so that at least a portion of the closure elements 816 and 817 are held between the side walls 821 and 822. Sidewalls 821 and 822 cooperate with the fastener strips 814 and 815 so that the fastener strips 814 and 15 are received between the side walls 821 and 822 as the slider moves between the open and closed position.

According to one embodiment, sidewalls 821 and 822 extend from a separating end of the slider to a pinching end of the slider, such that the side walls 21 and 22 are spaced farther apart at the separating end than at the pinching end. The closer spacing at the pinching end acts to pinch, or squeeze the fastening strips together, thereby forcing the closure element 816 and 817 into an interlocking relationship. A user can squeeze fastener strips together all at once, e.g., uppermost closure elements 816*a* and 817*a* are pressed together at approximately the same time that bottommost closure elements 816*b* and 817*b* are pressed together. Alternatively, the fastener strips can interlock by application of force in a rolling action along the length of the elongated slit.

A given fastener strip optionally comprises an additional structure for maintaining the slider in straddling relation with the fastener strips. In the embodiment of FIG. 8, the structure comprises a ridge 825 on the outer surface of a given fastener strips 814 and 15, and shoulders on the side walls of the slider. The shoulders project inwardly at a point at or below the closure elements 816 and 817. The shoulders act as structure that provides for maintaining the slider in a straddling relation with the fastener strips by grasping the lower surfaces of the ridges 825. The ridges 825 thus act as handles for the slider to hold onto, such that the slider 810 maintains the straddling relation with the fastener strips along the entire length of the elongated slit. Ridges 825 extend along the length of the outer surface of fastener strips 814 and 815 at a point at or below the closure elements and can be attached to the fastener strips by any desired means, such as, for example, by extruding with the fastener strips, heating, gluing, or snapping in place. The ridges can also result from the difference in thicknesses between a given fastener strip and the bag.

The slider 810 may be made in multiple parts and welded together or the parts may be constructed to be snapped together; the slider 810 may also comprise one piece construction. Fabrication of the slider can be in accordance with any desired method, such as, for example, injection-molding, extrusion, material deposit fabrication (3D printing) or any other suitable method known to those of ordinary skill in the art. The slider 810 can be molded from any suitable plastic such, for example, as nylon, polypropylene, polystyrene, polyketone, polybutylene terephthalate, high-density polyethylene, polycarbonate, or ABS. The slider can be clear, opaque, or colored. It should be noted by those of skill in the art FIGS. 1 through 8 are conceptual illustrations allowing for an explanation of the present invention. Those of skill in the art should understand that various aspects of the embodiments of the present invention could be implemented using different materials, fasteners and minor design modifications. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention.

In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A surgical device for assisting in the placement of a prosthetic implant within a surgical pocket of a patient, the surgical device comprising:
   One or more sheets of polymer shaped in the form of a conical frustum and in which a proximal end of the frustum is sealed and a distal end of the frustum is open, the frustum having an elongated slit extending from the distal end toward the proximal end and further having a single opening formed by the distal opening and the elongated slit, the opening configured to accept the prosthetic implant into an interior cavity of the frustum;
   a set of inter-lockable fastener elements disposed along opposing sides of the elongated slit, the set of inter-lockable fastener elements configured to seal the elongated slit such that the distal end remains open to allow for egress of the prosthetic implant for placement into the surgical pocket;
   a lubricious coating applied to the interior cavity of the frustum; and
   one or more surface active coatings applied to the interior cavity of the frustum, wherein movement of the prosthetic implant out of the frustum and across the one or more surface active coatings causes interaction between the prosthetic implant and the one or more surface active coatings to provide one or more benefits that the one or more surface active coatings offer.

2. The surgical device of claim 1, wherein the lubricious coating is water activated.

3. The surgical device of claim 1, wherein the lubricious coating comprises a hydrophilic gel that decreases a coefficient of friction of the inside surface of the bag.

4. The surgical device of claim 1, wherein a given one of the one or more surface active coatings comprises an antimicrobial coating.

5. The surgical device of claim 1, wherein a given one of the one or more surface active coatings comprises a heparin coating.

6. The surgical device of claim 1 in which a plurality of surface active coatings are applied simultaneously to the interior cavity of the frustum.

7. The surgical device of claim 6 in which a plurality of surface active coatings are applied simultaneously to the interior cavity of the frustum in conjunction with the lubricious coating.

8. The surgical device of claim 1, wherein the prosthetic implant is selected from the set of prosthetic implants consisting of a breast implant, a pectoral implant, a calf implant and a gluteal implant.

9. The surgical device of claim 1, wherein the one or more sheets of polymer are between 0.01 inches and 0.005 inches thick.

10. The surgical device of claim 9, wherein the one or more sheets of polymer comprises of one or more sheets of polymer selected from the set of polymers consisting of medical grade vinyl, medical grade PVC, medical grade nylon and polyethylene.

11. The surgical device of claim 1, wherein a ridge formed by the sealed elongated slit provides a support guide for the prosthetic implant during placement into the surgical pocket.

12. The surgical device of claim 1, comprising a marker on the bag to properly align the prosthetic implant for placement into the surgical pocket.

13. The surgical device of claim 1, comprising a plurality of size guide lines printed on the one or more sheets of polymer to properly align a cutting device for excision of excess material from the distal opening of the frustum.

14. The surgical device of claim 1, comprising a sheet of absorbable material placed within the interior cavity of the frustum that when exposed to a fluid allows the fluid to wick through the absorbable material and activate a lubricious coating on an inside surface of the bag.

15. The surgical device of claim 14 wherein the sheet of absorbable material changes color when exposed to the fluid.

16. The surgical device of claim 1 wherein the surface active coating comprises an antimicrobial component.

17. The surgical device of claim 16 wherein the surface active coating comprises a non-thrombogenic component.

* * * * *